US008556441B2

(12) United States Patent
Battle et al.

(10) Patent No.: US 8,556,441 B2
(45) Date of Patent: Oct. 15, 2013

(54) FRAGRANCE EMITTING ARTICLE

(76) Inventors: Matthew Battle, Louisville, KY (US);
Frederick Battle, Louisville, KY (US)

( * ) Notice: Subject to any disclaimer, the term of this patent is extended or adjusted under 35 U.S.C. 154(b) by 836 days.

(21) Appl. No.: 12/578,563

(22) Filed: Oct. 13, 2009

(65) Prior Publication Data

US 2010/0090021 A1     Apr. 15, 2010

Related U.S. Application Data

(60) Provisional application No. 61/105,149, filed on Oct. 14, 2008.

(51) Int. Cl.
*F21V 33/00* (2006.01)
(52) U.S. Cl.
USPC ............. 362/96; 362/161; 362/253; 362/351; 362/806; 239/34; 422/125; 428/905
(58) Field of Classification Search
USPC ........... 362/96, 157, 161, 253, 257, 351, 358, 362/806, 810; 239/34; 422/125; 428/905
See application file for complete search history.

(56) References Cited

U.S. PATENT DOCUMENTS

| 2,792,491 | A | * | 5/1957 | Rand | ............................... 108/23 |
| 3,898,039 | A | * | 8/1975 | Lin | ............................... 422/125 |
| 2004/0095754 | A1 | * | 5/2004 | Hsu | ............................... 362/161 |
| 2008/0207481 | A1 | * | 8/2008 | Meine et al. | ...................... 512/4 |

* cited by examiner

*Primary Examiner* — Stephen F Husar
*Assistant Examiner* — Meghan Dunwiddie
(74) *Attorney, Agent, or Firm* — The Law Office of Jerry D. Haynes

(57) ABSTRACT

The present invention relates to a fragrance emitting article in the form of a lamp shade comprising: an outer surface, where at least one fragrance is applied to the outer surface; and an inner surface, where at least one fragrance is applied to the inner surface. In one exemplary embodiment, the lamp shade includes a pyramidal structure that includes an open top having a periphery and an open base having a periphery. A supporting frame maintains the pyramidal structure, where the supporting frame is coupled with the periphery of the structure at the open top and the open base.

Figure 1:
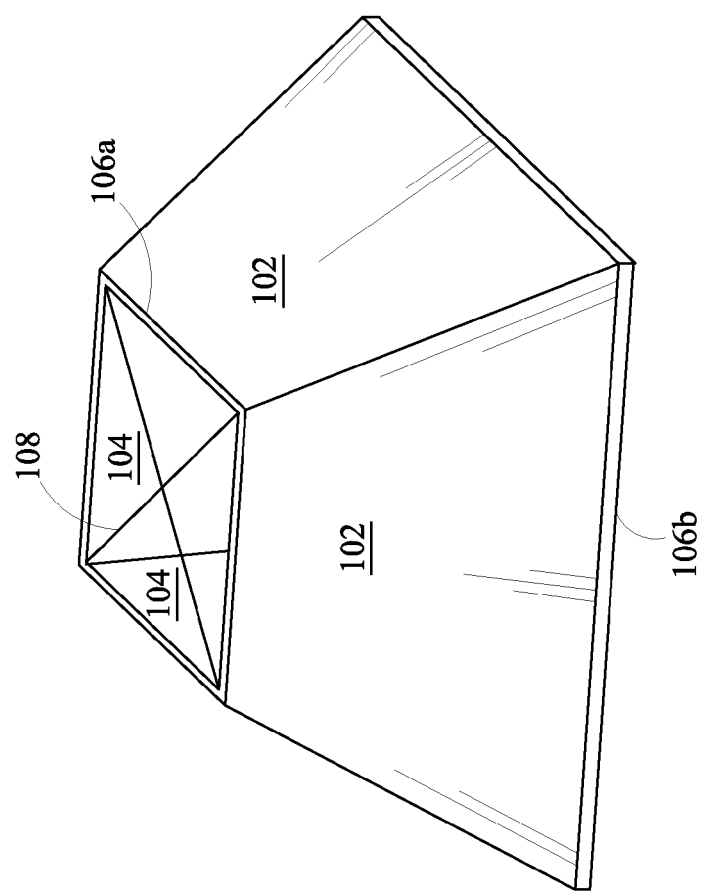

11 Claims, 2 Drawing Sheets

FRAGRANCE EMITTING ARTICLE

CROSS REFERENCE TO OTHER APPLICATIONS

This application claims priority to U.S. Provisional Application Ser. No. 61/105,149 filed on Oct. 14, 2008.

I. FIELD OF THE INVENTION

The present invention generally relates to a fragrance emitting article, and more specifically to an inconspicuous article that emits fragrance.

II. MOTIVATION FOR THE INVENTION

People throughout ages have been using various fragrance emitting substances for enhancing the fragrance of ambient air. The fragrance emitting substances may be natural, such as flowers, certain natural oils, and the like, or man-made, such as artificial perfumes.

Various artificial fragrance emitting substances exist in the market today for assisting people in spreading and maintaining a fragrant atmosphere in an area, such as a bedroom, a bathroom or a guest room, in which they may be present. Such fragrance emitting substances may be available in the form of fragrance emitting articles, such as air fresheners, scented candles, deodorants, oil lamps, carpet fresheners, poppers, automatic air wicks, and the like. A fragrance emitting article may be placed in the area where the fragrance is desired and after a period of time, a fragrant atmosphere is formed, thereby causing a pleasant smelling experience for the people in the area.

However, certain inherent drawbacks exist in the fragrance emitting articles of the prior art. Some of the fragrance emitting articles, such as air fresheners, poppers, automatic air wicks and scented candles, are capable of emitting the fragrance for a limited duration only. Such articles need to be frequently replaced or replenished with fragrance emitting substances, in order to maintain the fragrance in the area. Certain other fragrance emitting articles, such as oil lamps and scented candles, may cause potentially dangerous situations when in use, as they require a fire to be lit for the fragrance to spread into the air. The fire may cause an accident in the area if the fire comes in contact with flammable materials that may be present in the area. Further, such fragrance emitting articles may be expensive. Furthermore, some of the fragrance emitting articles may be cumbersome to use, such as carpet fresheners. Still further, some of the fragrance emitting articles may be noticeable to the people in the area where the fragrance is being maintained. Such articles may not have an aesthetic appeal, thereby making their presence undesirable.

Consequently, a need for a fragrance emitting article, without the drawbacks of the prior art, capable of emitting fragrance for a substantial amount of time still exists. Further, the fragrance emitting article needs to be safe, cost effective and easy to use. Furthermore, it is desirable that the fragrance emitting device be inconspicuous and have an aesthetic appeal.

Accordingly, it is an object of the present invention to obviate the above and other disadvantages from existing art and to provide a fragrance emitting article for spreading and maintaining fragrance in a specific area for a substantial duration of time. It is further an object of the present invention to provide a fragrance emitting article that is safe, cost effective and easy to use. Furthermore, it is an object of the present invention to provide a fragrance emitting article that is inconspicuous. Still further, it is an object of the present invention to provide a fragrance emitting article that is aesthetically appealing.

III. SUMMARY OF THE INVENTION

The present invention relates to a fragrance emitting article in the form of a lamp shade comprising: an outer surface, where at least one fragrance is applied to the outer surface; and an inner surface, where at least one fragrance is applied to the inner surface. In one exemplary embodiment, the lamp shade includes a pyramidal structure that includes an open top having a periphery and an open base having a periphery. A supporting frame maintains the pyramidal structure, where the supporting frame is coupled with the periphery of the structure at the open top and the open base.

In another exemplary embodiment, the supporting frame of the lamp shade is coupled to a lamp support of a lamp at the open base of the pyramidal structure. A bulb may be coupled to the lamp support, where the bulb emits light and dissipates heat. The heat from the bulb accentuates the at least one fragrance applied on the lamp shade. The fragrances emitted by the fragrance emitting article may include terpene-free fragrances, where said terpene-free fragrances produce a pleasant aroma that may last for at least six months.

IV. DESCRIPTION OF THE DRAWINGS

Figure 2:
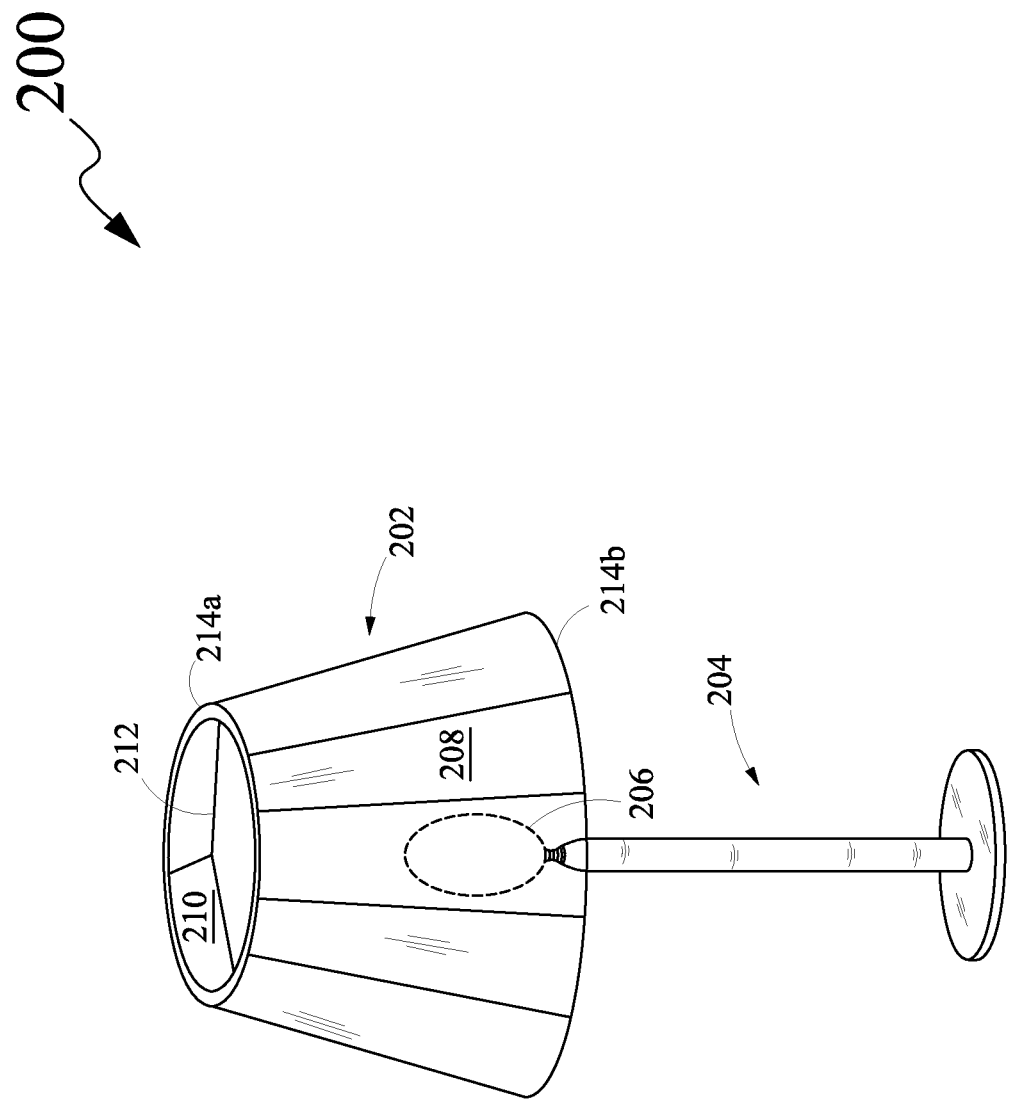

The advantages and features of the present invention will become better understood with reference to the detailed description taken in conjunction with the accompanying drawings, in which:

FIG. 1 depicts a perspective view of a fragrance emitting lampshade, in accordance with an exemplary embodiment of the present invention; and FIG. 2 depicts a perspective view of a lamp with another exemplary embodiment of the fragrance emitting lampshade in accordance with the present invention.

Like reference numerals refer to like parts throughout the description of several views of the drawings.

V. DESCRIPTION OF THE INVENTION

The best mode for carrying out the invention is presented in terms of its preferred embodiments, herein depicted in FIGS. 1 and 2. The preferred embodiments described here in detail for illustrative purposes, are subject to many variations. It is understood that various omissions and substitutions of equivalents are contemplated as circumstances may suggest or render expedient, but are intended to cover the application or implementation without departing from the spirit or scope of the present invention.

The terms "a" and "an" herein do not denote a limitation of quantity, but rather denote the presence of at least one of the referenced item.

The present invention provides a fragrance emitting article for emitting and maintaining a fragrance in ambient air. The fragrance emitting article may be placed in a bedroom, a bathroom, a guest room, and the like. Although the present invention is presented in the form of a lampshade that is commonly present in most homes and offices, it will be apparent to a person skilled in the art that the lampshade is only an exemplary embodiment and the fragrance emitting article may be any other article that meets the needs of the present invention.

As illustrated in FIG. 1, the present invention provides a perspective view of a lamp shade 100 that is heavily scented with at least one fragrance. Exemplary fragrances include natural fragrances, such as rose, sandalwood, strawberry, and the like, or artificial fragrances. The fragrance may be obtained from a fragrance emitting substance, such as flowers, natural oils, artificially prepared perfumes, and the like. As shown in FIG. 1, the lamp shade 100 includes an outer surface 102 and an inner surface 104. The fragrance may be applied on the outer surface 102 of the lamp shade 100 and another fragrance or the same fragrance may be applied on the inner surface 104 of the lamp shade 100.

In one exemplary embodiment of the present invention, the lamp shade 100 may be structured as a frustum of a pyramid, as depicted in FIG. 1 (hereinafter, the frustum of the pyramid will be referred to as 'pyramidal structure'). The pyramidal structure includes an open top having a periphery 106a and an open base having a periphery 106b. The pyramidal structure of the lamp shade 100 may be maintained by a supporting frame 108. The supporting frame 108 is coupled with the periphery 106a of the pyramidal structure at the open top. Similarly, the supporting frame 108 is coupled with the periphery 106b of the pyramidal structure at the open base (not shown). The supporting frame 108 is also coupled with the open base 106b of the pyramid structure along a periphery of the open base 106b. Further, the supporting frame 108 may be made of a rigid material, such as metal, wood, and the like. Furthermore, the supporting frame 108 may be covered with a fabric, such as cotton, polyester, and the like. A surface of the supporting frame 108 covered with the fabric forms the inner surface 104 of the lamp shade 100 and an opposite surface of the fabric forms the outer surface 102 of the lamp shade 100.

Alternatively, the pyramidal structure of the lamp shade 100 may be maintained by a stiff material, such as a board, plywood, and the like, of the lamp shade 100. The stiff material may form the inner surface 104 and may be covered with a fabric, such as cotton, polyester, silk, and the like, that may form the outer surface 102 of the lamp shade 100.

In an embodiment, a fragrance of the at least one fragrance may be applied on sidewalls of the pyramidal structure of the lamp shade 100. Alternatively, the at least one fragrance may be applied on the outer surface 102 and the inner surface 104, as mentioned earlier. It will be apparent to a person skilled in the art that the lamp shade 100 may be of any other three dimensional structure, such as a cuboid, a cone, an octahedron, a cylinder, a hemi-sphere, and the like.

Referring now to FIG. 2, a perspective view of a lamp 200 with a lamp shade 202 is shown, in accordance with another embodiment of the present invention. The lamp 200 includes a lamp support 204 and a bulb 206. The lamp shade 202 includes an outer surface 208, an inner surface 210 and a supporting frame 212. The at least one fragrance may be applied on the outer surface 208 and the inner surface 210 of the lamp shade 202. The lamp shade 202 is structured as a frustum of a cone with an open top and an open base (hereinafter, the frustum of the cone will be referred to as 'conical structure'). The frustum of the cone includes a periphery 214a along the open top of the frustum and a periphery 214b along the open base of the frustum.

The conical structure of the lamp shade 202 may be maintained by the supporting frame 212. The supporting frame 212 is similar to the supporting frame 106 explained in FIG. 1. The supporting frame 212 of the lamp shade 202 is coupled to the periphery 214a of the conical structure, as shown in FIG. 2. Further, the supporting frame 212 is coupled to the periphery 214b of the conical structure (not shown).

The conical structure of the lamp shade 202 may also be maintained by using a stiff material, such as a board, plywood, and the like. As explained in FIG. 1, the stiff material may form the inner surface 210 and may be covered with a fabric, such as cotton, polyester, silk, and the like, that may form the outer surface 208 of the lamp shade 202. The fabric may be capable of absorbing a fragrance of the at least one fragrance. Further, the fabric may be capable of retaining the fragrance for a substantial amount of time.

The supporting frame 212 of the lamp shade 202 is coupled to the lamp support 204 of the lamp 200 at the open base of the conical structure (not shown). Though, coupling between the lamp support 204 and the supporting frame 212 is not shown, it will be evident to a person skilled in the art that the coupling may be performed by any existing method, such as welding, coupling by nut and bolt arrangement, sticking, and the like. Further, it will be evident to a person skilled in the art that the lamp support 204 may be configured to have any other shape that is capable of supporting the lamp shade 202 therein.

Further, the bulb 206 is coupled to the lamp support 204 at an end portion of the lamp support 204, as shown in FIG. 2 (in dotted). It will be evident to a person skilled in the art that the lamp 200 includes a power supply and other requisite electrical connections so that the bulb 206 may dissipate light in a specific area where the lamp 200 is placed.

When in use, the bulb 206 of the lamp 200 glows due to the electrical connections and dissipates light, as well as heat. The heat from the bulb 206 accentuates the at least one fragrance applied on the lamp shade 202, thereby causing a pleasant smelling experience for people in a specific area, such as a bedroom, a dining room, and the like. When not in use, the lamp 200 may dissipate the at least one fragrance applied on the lamp shade 202 in the area causing a pleasant aroma to spread in the area. Further, since the at least one fragrance may be applied on the lamp shade 100 or the lamp shade 200, origin of the at least one fragrance that spreads in the area will be inconspicuous to the people.

In an embodiment of the present invention, a pattern, such as vertical stripes, may be present on an outer surface, such as the outer surface 208, of a lamp shade, such as the lamp shade 202 of FIG. 2, and may be available in various colors that may enhance a visual appeal of the lamp shade.

In another embodiment of the present invention, the lamp shade, such as the lamp shade 202 or the lamp shade 100, may be available with terpene-free fragrances that produce pleasant aroma and that may be capable of providing the aroma for a substantial amount of time, such as six months or more.

In still another embodiment of the present invention, the fabric used for the lamp shade may be fire resistant and self extinguishing, such as silk or wool.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The exemplary embodiment was chosen and described in order to best explain the principles of the invention and its practical application, to thereby enable others skilled in the art to best utilize the invention and various embodiments with various modifications as are suited to the particular use contemplated.

What is claimed is:
1. A fragrance emitting article in the form of a lamp shade comprising:

a. an outer surface, where at least one terpene-free fragrance is applied to the outer surface, where the at least one terpene-free fragrance produces an aroma for at least six months;
b. an inner surface, where at least one terpene-free fragrance is applied to the inner surface, where the at least one terpene-free fragrance produces an aroma for at least six months.

2. The fragrance emitting article according to claim 1, where the lamp shade includes a pyramidal structure, where said structure includes an open top having a periphery and an open base having a periphery.

3. The fragrance emitting article according to claim 2, where a supporting frame maintains said pyramidal structure, where said supporting frame is coupled with the periphery of the structure at the open top and the open base.

4. The fragrance emitting article according to claim 3, where the supporting frame is made of a rigid material, said rigid material including at least one of a metal and wood.

5. The fragrance emitting article according to claim 3, where the supporting frame is covered with a fabric, said fabric including at least one of cotton and polyester and said fabric forms the inner surface an outer surface of the lamp shade.

6. The fragrance emitting article according to claim 2, where said pyramidal structure is maintained by a stiff material, where said stiff material includes a board and a plywood and said stiff material is covered by a fabric where said fabric includes at least one of a cotton, polyester and silk, said fabric forms the outer surface of the lamp shade.

7. The fragrance emitting article according to claim 1, where the lamp shade forms a three dimensional structure, where said structure includes at least one of a cuboid, a cone, an octahedron, a cylinder and a hemi-sphere.

8. The fragrance emitting article according to claim 3, where the supporting frame of the lamp shade is coupled to a lamp support of a lamp at the open base of the pyramidal structure.

9. The fragrance emitting article according to claim 8, where a bulb is coupled to the lamp support.

10. The fragrance emitting article according to claim 9, where the bulb of the lamp emits light and dissipates heat, where the heat from the bulb accentuates the at least one fragrance applied on the lamp shade.

11. The fragrance emitting article according to claim 1, where the at least one fragrance includes terpene-free fragrances, where said terpene-free fragrances produce a pleasant aroma, and the aroma is emitted for at least six months.

* * * * *